United States Patent [19]

Gordon et al.

[11] Patent Number: 4,874,582
[45] Date of Patent: Oct. 17, 1989

[54] SAMPLE HANDLING UNIT FOR CENTRIFUGATION

[75] Inventors: Alan J. Gordon, Liverpool; Donald G. Billington, Stoke on Trent, both of England

[73] Assignee: Shandon Scientific Limited, Runcorn, England

[21] Appl. No.: 109,584

[22] Filed: Oct. 19, 1987

Related U.S. Application Data

[63] Continuation-in-part of Ser. No. 871,081, Jun. 5, 1986, abandoned.

[30] Foreign Application Priority Data

Jun. 10, 1985 [GB] United Kingdom ............... 8514590

[51] Int. Cl.$^4$ ............................................ G01N 35/00
[52] U.S. Cl. ...................................... 422/102; 422/64; 422/72; 436/45; 494/16
[58] Field of Search ............................ 422/64, 72, 102; 436/45; 118/52; 427/2, 4; 494/16, 20; 210/361

[56] References Cited

U.S. PATENT DOCUMENTS

| | | | |
|---|---|---|---|
| 4,197,329 | 4/1980 | Holyrod et al. | 427/2 |
| 4,280,442 | 7/1981 | Johnson | 118/52 |
| 4,391,710 | 7/1983 | Gordon | 210/361 |
| 4,469,793 | 9/1984 | Guigan | 436/45 |
| 4,557,600 | 12/1985 | Klose et al. | 436/45 |
| 4,812,294 | 3/1989 | Combs | 422/72 |

Primary Examiner—Michael S. Marcus
Assistant Examiner—D. John Griffith, Jr.
Attorney, Agent, or Firm—Vaden, Eickenroht, Thompson & Boulware

[57] ABSTRACT

A sample handling unit for centrifugation apparatus, especially for cytocentrifugation to produce cell monolayers is disclosed. The sample handling unit is adapted for automated protective processing, e.g. fixation, of matter deposited on a slide during the centrifugation operation. For this purpose the unit has a body defining a deposition chamber, and a treatment fluid reservoir communicating with the deposition chamber via a buffer chamber and a flow path including a weir so arranged that in the position for centrifugation, treatment fluid such as fixative placed in the reservoir is retained therein until centrifugation produces an artificial gravitational field that causes the fluid to flow to the buffer chamber in which it is then retained by the weir for so long as the artificial gravitational field is maintained. Upon decay of that field the fluid flows over the weir towards the deposition chamber. There may be a series of such reservoirs and associated buffer chambers and weirs in respective flow paths or in an extended flow path through which flow path or paths a succession of treatment fluids are caused to progress in sequence by repeatedly applying the artificial gravitational field. There may also be a sample reservoir that communicates with the deposition chamber in a manner providing for transfer of sample material from this reservoir to the deposition chamber only when the artificial gravitational field is applied.

8 Claims, 8 Drawing Sheets

Fig. 15.
Fig. 16.
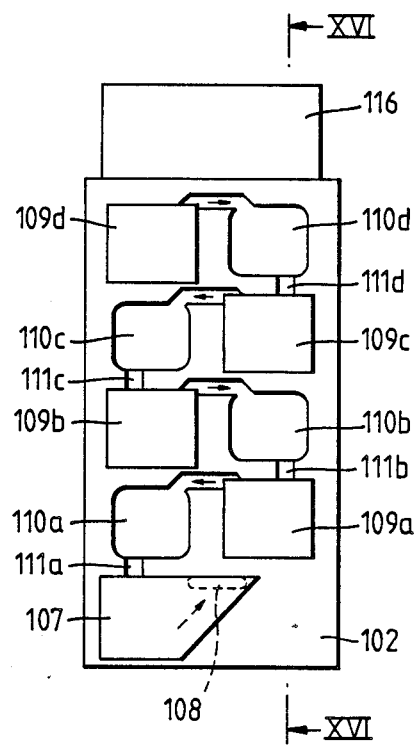
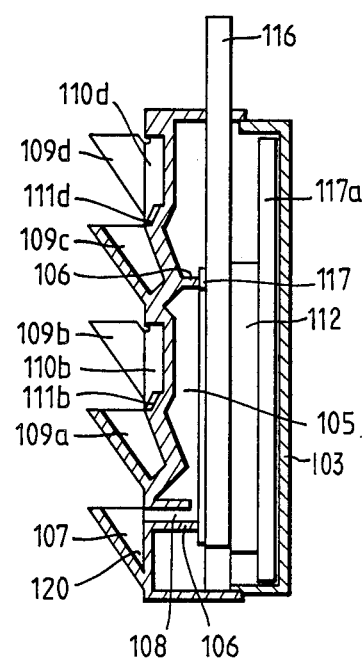

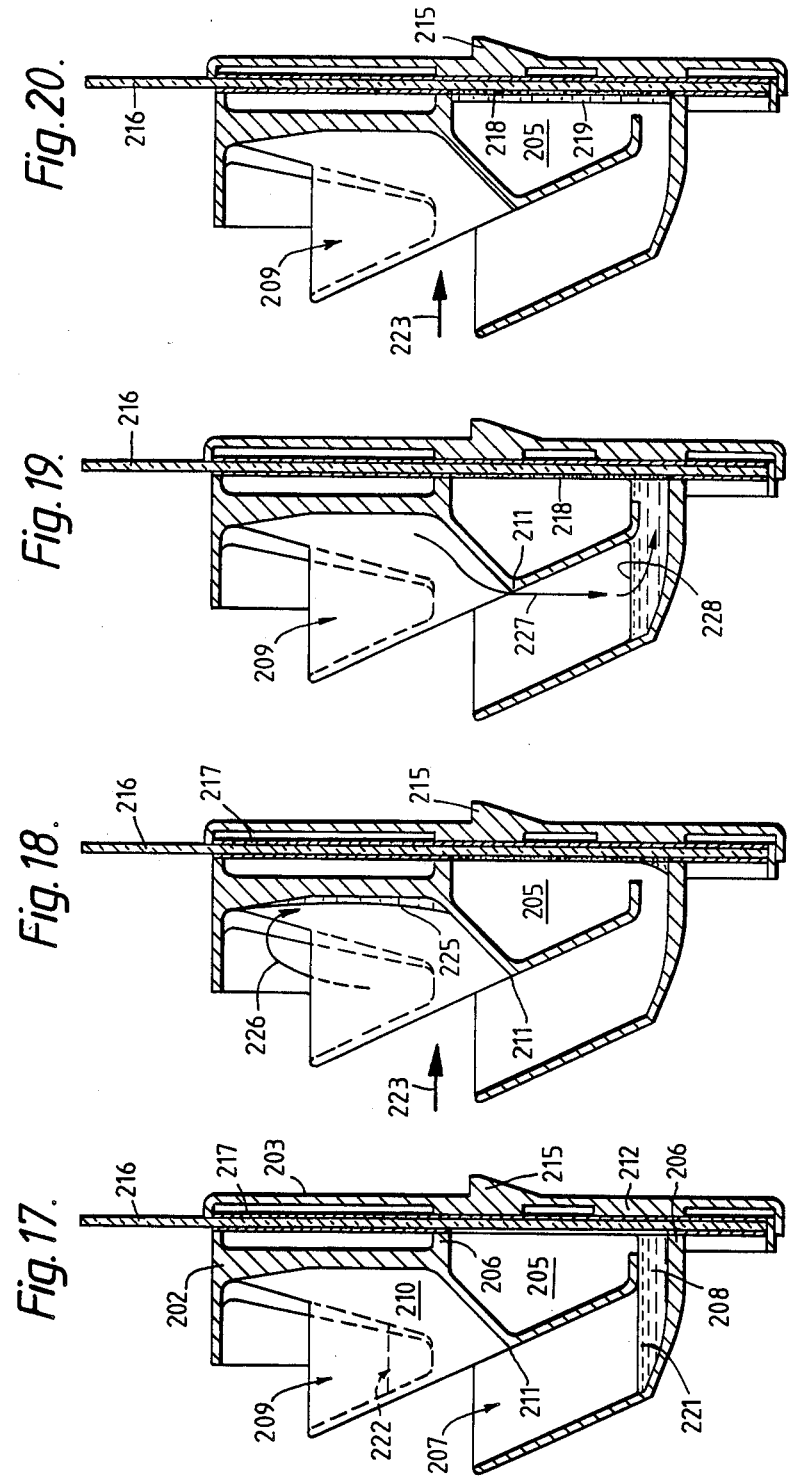

SAMPLE HANDLING UNIT FOR CENTRIFUGATION

RELATED APPLICATION

This Application is a continuation-in-part of application Ser. No. 871,081 filed June 5, 1986, for "Centrifugation", now abandoned.

FIELD OF THE INVENTION

This invention concerns the centrifugation of suspensions to effect separation of solids therefrom for, e.g., microscopic examination. The invention is especially concerned with the centrifugation of body fluid and like samples comprising cell suspensions to accomplish the deposition of a cell layer on a slide or other receiving surface for cytological examination, a general objective of the invention being to facilitate and improve the preparation of such cell layers in routine cytological screening procedures, e.g., in the screening of cervical cell samples for carcinoma.

BACKGROUND TO THE INVENTION AND THE PRIOR ART

It is known to place a cell suspension in a generally tubular sample chamber having an open end juxtaposed to the surface of a microscope or like slide, with the interposition of an apertured filter card that both provides a seal between the sample chamber and the slide surface and also serves to absorb the liquid components of the suspension. The assembly of sample chamber, slide and filter card is subjected to centrifugation to cause the deposition of a layer of cells on the slide surface and the removal of the suspension liquid into the filter card. One example of cytocentrifugation apparatus especially adapted to perform this cell separation and deposition technique is disclosed in U.S. Pat. No. 4,391,710. U.S. Pat. No. 4,576,110 discloses a similar technique which, however, replaces the filter card with an absorbent plug communicating with a deposition area on the slide.

Prior to microscopic or like examination, the deposited cell layer on the slide requires at least fixation and may also require staining or other procedures to be applied thereto. Hitherto, any such after-treatment of the deposited cell layer has been accomplished after the centrifugation operation has been concluded and the assembly of sample chamber and slide has been dismantled to permit the slide and the cell layer deposited thereon to be recovered for such further processing and subsequent examination, the further processing—e.g. fixation—being effected by conventional manual or automated techniques for such purposes.

The freshly deposited cell layer on the slide is vulnerable to damage and degradation by handling and delay between its deposition and the subsequent processing treatment to which it is subjected. In a busy laboratory handling many such cell deposits by automated or semi-automated techniques, the making up of batches of slides bearing freshly deposited cell layers for such processing carries with it a substantial risk of damage and degradation of individual cell deposits.

A more specific objective of the present invention is therefore to provide for accomplishing at least one protective treatment of a freshly deposited cell layer as an adjunct to the centrifugation procedure and prior to any dismantling of the assembly of sample chamber and slide and, indeed, with the minimum disturbance of the assembly.

SUMMARY OF THE INVENTION

In accordance with the invention, a sample handling unit for a centrifugation apparatus comprises a body having means therein defining a sample chamber adapted to receive fluent sample material when the body is in a position for centrifugation. The sample chamber includes a deposition chamber having an open side arranged to be juxtaposed to a receiving surface for depositing thereon sample material under the influence of an artificial gravitational field. The body further has means defining a treatment fluid reservoir, a buffer chamber and a flow path communicating the buffer chamber with the sample chamber and including a weir that permits flow in the flow path only in the substantial absence of the artificial gravitational field.

The arrangement is such that with the sample handling unit in its position for centrifugation—for instance when supported on a centrifuge head as an assembly of sample handling unit, receiving surface and filter card—treatment fluid placed in the treatment fluid reservoir will be retained therein until centrifugation creates an artificial gravitational field appropriate to centrifugation of a fluent sample, such as a cell suspension in the deposition chamber. Under the influence of this artificial gravitational field, the treatment fluid will be transferred from the reservoir to the buffer chamber to remain therein for so long as the artificial gravitational field persists. However, when the artificial gravitational field decays and normal gravity thereafter acts on the treatment fluid in the buffer chamber, the fluid therein will flow over the said weir and to the sample chamber. If during the preceding centrifugation that led to the transfer of the treatment fluid from the reservoir to the buffer chamber, the solids of a suspension in the deposition chamber were separated and deposited on to the receiving surface and the liquid of the suspension were absorbed to leave an essentially dry layer of solids on the receiving surface, the subsequent entry of treatment fluid into the deposition chamber will be effective to bring that fluid into contact with the deposited solids. The treatment fluid may, for instance, be a fixative appropriate to fix the disposition and properties of the solids on the receiving surface.

Preferably the sample chamber also comprises a sample reservoir having flow path connection to the deposition chamber arranged to permit flow of material from the sample reservoir to the deposition chamber only under the influence of an artificial gravitational field appropriate to centrifugation of such material in the deposition chamber. Such an arrangement can be effective to prevent normal gravity, and/or translational acceleration fields during run-up of the centrifuge to create the artificial gravitational field for centrifugation, from affecting the sedimentation of solids in a suspension sample and leading to nonuniformity in the deposited solids layer on the receiving surface.

In this connection it is known from said U.S Pat. No. 4,391,710 to retain a cell suspension in a sample reservoir prior to the establishment of the centrifugation artificial gravitational field, for the purposes indicated, but in the arrangement of said Patent transfer of material from the sample reservoir to the deposition chamber results from a change in position of the sample chamber and associated sample reservoir under the influence of the artificial gravitational field.

While for the reasons indicated it is preferred that the sample chamber include a sample reservoir from which material is transferred to the deposition chamber only when the artificial gravitational field is established as will be described below, the invention is applicable to arrangements not having such a sample reservoir, or having a sample reservoir from which material can transfer to the deposition chamber under normal gravity.

In use of centrifugation apparatus having sample handling units in accordance with the invention, the removal of treatment fluid from contact with solids on the receiving surface may be accomplished by absorption of such fluid into the filter card or other absorbent. Such absorption may be promoted, and the risk of dislodgement of deposited solids minimised, by running-up the centrifuge to restore an artificial gravitational field acting normal to the receiving surface. In preferred embodiments, in which the sample chamber of the unit has a sample reservoir from which material is transferred to the deposition chamber under the influence of the artificial gravitational field, the flow path means preferably also include the sample reservoir so that treatment fluid flows first to the sample reservoir and is transferred from this to the deposition chamber only under the influence of a restored artificial gravitational field. This further minimises the risk of dislodgement of deposited solids by uncontrolled flow of treatment fluid in the deposition chamber. However, even when the sample chamber of the unit includes a sample reservoir, the flow path for treatment fluid from the buffer chamber may be direct to the deposition chamber.

Two or more treatment fluids may be fed successively to the deposition chamber of a sample handling unit in the course of centrifugation. Thus a second treatment fluid may be introduced into the treatment fluid reservoir at the conclusion of an initial centrifugation step that has, as above explained, resulted in the transfer of a first treatment fluid from the treatment fluid reservoir into the said buffer chamber. A second centrifugation step will then cause both expulsion of the first treatment fluid from the deposition chamber into the absorbent and the transfer of the second treatment fluid to the buffer chamber for subsequent movement into the deposition chamber when this second centrifugation step is terminated. Further treatment fluids may be introduced into the treatment fluid reservoir with intermediate centrifugation steps to accomplish their transfer in succession to the buffer chamber and then to the deposition chamber.

Moreover, to facilitate the sequential use of two or more treatment fluids, the sample handling unit may comprise two or more treatment fluid reservoirs associated with individual buffer chambers and weirs so arranged that the reservoir for a second or subsequent treatment fluid communicates with the deposition chamber via an extended flow path comprising a succession of buffer chambers and associated weirs so that transfer of fluid from this reservoir to the deposition chamber requires the establishment of an artificial gravitational field to transfer the treatment fluid to a first buffer chamber: the decay of that field to permit the transfer of the fluid over a weir to a second buffer chamber: the re-establishment of the artificial gravitational field to accomplish transfer of the fluid to a third buffer chamber: and so on, the fluid flowing eventually the deposition chamber when the artificial gravitational field decays after a number of transfers of the fluid appropriate to its rank in the number of treatment fluids for which reservoirs are provided. There may be individual flow paths to the deposition chamber from the respective treatment fluid reservoirs, or a single extended flow path comprising all the treatment fluid reservoirs and buffer chambers.

The body of the sample handling unit with its deposition chamber, associated treatment fluid reservoir(s) and buffer chamber(s) may conveniently be formed as a moulding of suitable plastics material.

The sample handling unit of this invention may conveniently and desirably be utilised in conjunction with the invention of patent application Ser. No. 871,061 filed June 5, 1986 (now U.S. Pat. No. 4,696,743) and with centrifugation apparatus as disclosed in co-pending patent application Ser. No. 871,530 filed June 6, 1986.

BRIEF DESCRIPTION OF THE DRAWINGS

FIGS. 14, 15 and 16 are respectively a front three-quarter perspective view, a diagrammatic front elevation and a section on line XVI—XVI of FIG. 15, of a further embodiment of a sample handling unit in accordance with the invention; and FIGS. 17, 18, 19 and 20 correspond with FIGS. 5, 6, 7 and 8 respectively, but illustrate stages in the use of a modified form of the embodiment of the sample handling unit of FIGS. 1 to 4.

DESCRIPTION OF PREFERRED EMBODIMENTS OF THE INVENTION

Figure 1:
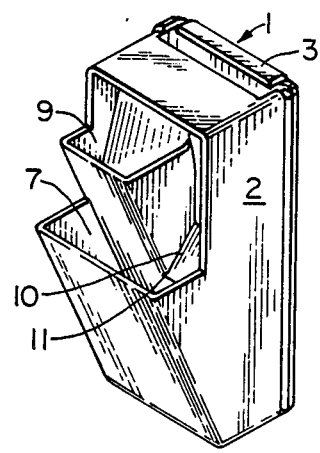
FIG. 1 is a front three-quarter perspective view of the embodiment of a sample handling unit embodying the invention.
Figure 2:
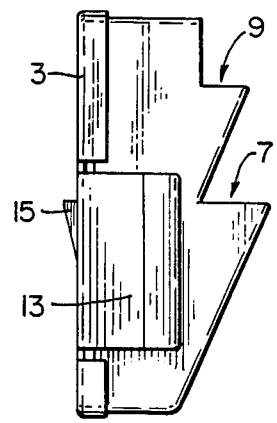
FIG. 2 is a side elevation of the sample handling unit of FIG. 1.
Figure 3:
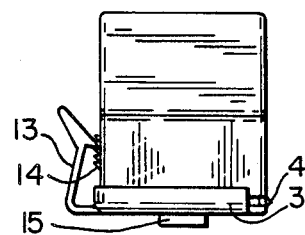
FIG. 3 is an underneath plan of the unit of FIG. 1.
Figure 4:
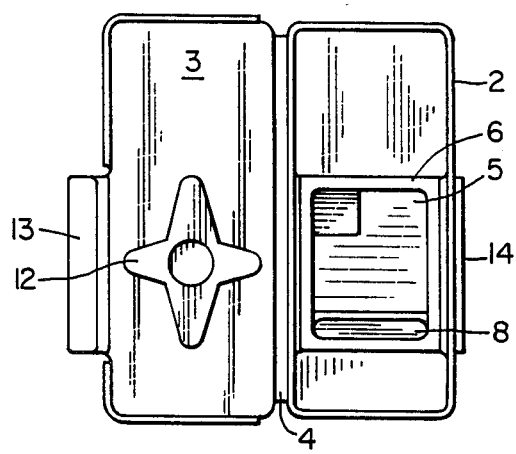
FIG. 4 is a rear view of the sample handling unit with its rear door in the open condition.

FIGS. 1 to 4 illustrate one form of sample handling unit embodying the invention. The unit shown therein generally at 1 in these Figures has a body, conveniently formed as a moulding of a suitable plastics material that may be translucent or transparent to facilitate observation of materials contained therein, comprising a main body part 2 and a rear door 3 joined to the body part 2 by an integral plastics hinge 4.

The unit 1 includes a sample chamber having a deposition chamber 5 that is generally rectangular in vertical section as seen in the drawings and that is defined at its rear end by a wall 6 that projects slightly to the rear of the body part 2 to constitute a rectangular frame-like rib. The sample chamber includes a sample reservoir 7 that communicates with the deposition chamber 5 via a slot 8.

The unit 1 further comprises a treatment fluid reservoir 9 with an associated buffer chamber 10 having a wall that constitutes a weir 11 over which fluid may pass from the buffer chamber 10 to the sample reservoir 7, and thence to the deposition chamber 5, in a manner to be explained.

The rear door 3 is formed with a cruciform pressure pad 12 and a latch 13 that engages a set of dog teeth 14 on the side of the body part 2 to secure the rear door in its closed condition. The rear face of the rear door 3 also has a tang 15 for co-operation with a centrifuge head carrier bucket as will be described.

The enlarged sectional views of FIGS. 5 to 8 illustrate the internal construction of the sample handling unit 1 as well as the manner in which materials placed in its sample reservoir 7 and in its treatment fluid reservoir 9 are transferred in sequence to the deposition chamber 5 during a centrifugation operation. These Figures also show the sample handling unit assembled with a glass microscope slide 16 enwrapped with a folded filter card 17 that is formed with a rectangular aperture corresponding in shape with the deposition chamber section as defined within the wall 6 so as to expose and define a corresponding deposit-receiving surface area of the slide 16, the filter card 17 at the margin of this aperture being trapped between the projecting end of the wall 6 and the slide 16 so as to form a seal between the slide and the the deposition chamber 5.

In use of the sample handling unit 1 as so far described, the unit is assembled with a slide 16 and filter card 17 and the rear door 3 closed to secure the slide and filter card in place with the pressure pad 12 on the door holding the slide and card firmly against the rear end of the wall 6. The assembly is then suitably fitted to a centrifuge head in the upright attitude illustrated in FIGS. 5 to 8 and with its rear door 3 radially outwards in relation to the axis of rotation.

A fluent, e.g. cell suspension, sample introduced into the sample reservoir 7 while the centrifuge is at rest collects under normal gravity in a well 20 at the lower end of the reservoir 7 below the level of the slot 8. Accordingly, while the centrifuge is at rest the sample material remains in the well 20.

Figure 5:
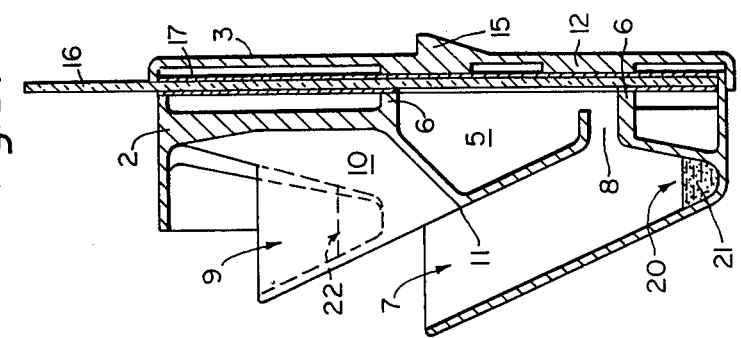
FIGS. 5, 6, 7 and 8 are enlarged vertical sectional views of the sample handling unit of FIG. 1 fitted with a slide and filter card and illustrating successive stages in use of this unit in centrifugation apparatus.

A treatment fluid, such as a fixative, placed in the treatment fluid reservoir 9 while the centrifuge is at rest likewise remains in the reservoir 9 while the centrifuge is at rest. FIG. 5 illustrates this state of affairs with the sample shown at 21 and the treatment fluid level indicated at 22.

Figure 6:
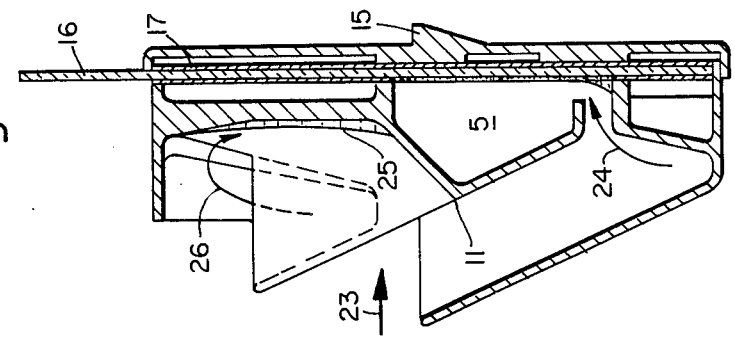

When now the centrifuge is run up so that the normal vertical gravitational field is replaced by an artificial gravitational field acting horizontally and radially outwardly of the axis of rotation, i.e. in the direction of arrow 23 (FIG. 6), the sample material is caused to flow from the well 20 into the deposition chamber 5 to form a layer over the exposed deposit-receiving surface of the slide 16, the sample passing through the slot 8 as represented by the arrow 24 in FIG. 6. At the same time the treatment fluid that was in the reservoir 9 flows under the influence of the artificial gravitational field into the buffer chamber 10 where it is held as a layer 25 on the rear wall thereof, flowing to this position by the path indicated by the arrow 26.

While the artificial gravitational field is maintained, the denser components, e.g. solids, of the sample material segregate and are deposited on the deposit-receiving surface of the slide 16 while the liquid of the sample is absorbed in the filter card 17. Preferably the available cross-sectional area in the filter card for flow of this liquid away from the boundary of the aperture that defines the deposit-receiving area is restricted in the manner disclosed in application Ser. No. 871,061 filed June 6, 1986 (now U.S. Pat. No. 4,696,743) in order to ensure the formation of a uniform layer of solid on the deposit-receiving surface and as more fully explained in said Application.

Figure 7:
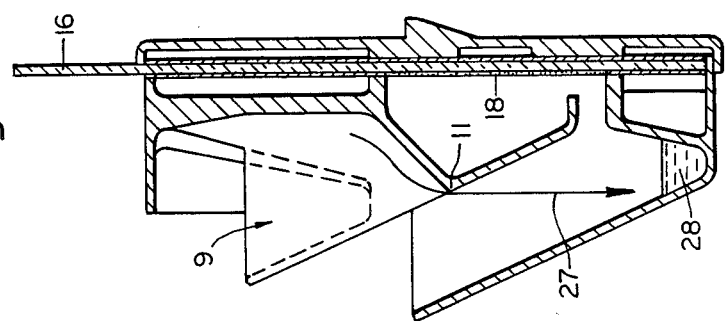

When the artificial gravitational field has been maintained for the appropriate period to accomplish deposition of the solids and the removal of the sample liquid to the filter card, the centrifuge is slowed to rest so that the artificial gravitational field disappears and normal gravity thereafter acts upon the sample handling unit. This results in the treatment fluid, that was transferred from the reservoir 9 to the buffer chamber 10 by the artificial gravitational field 23, now flowing over the weir 11 to fall into the well 20 of the sample reservoir 7. This flow is represented in FIG. 7 by the arrow 27, the treatment fluid in the well 20 being shown at 28. The layer of deposited solids on the slide 16 is shown at 18.

The treatment fluid is now caused to flow into the deposition chamber 5 by again running-up the centrifuge, to restore the artificial gravitational field represented by arrow 23. As indicated in FIG. 8, under the influence of this field, the treatment fluid flows in the path represented by arrow 29 to form a layer 19 over the deposited solids 18 on the slide 16 to accomplish a treatment thereof—e.g. fixation—before this fluid eventually flows out of the deposition chamber 5 by absorption into the filter card 17 in the same way that the liquid of the sample was removed from the deposition chamber during the previous centrifugation step described in relation to FIG. 6.

Figure 8:
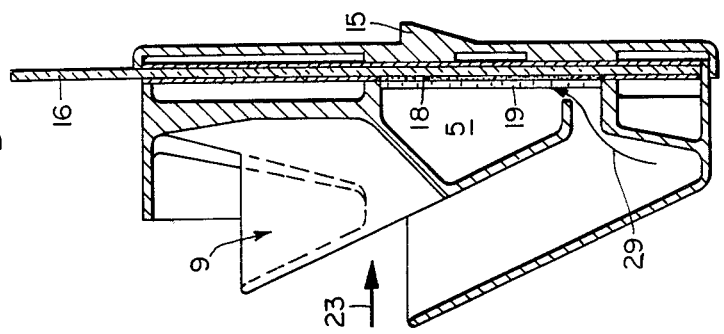

It should be understood that if treatment of the deposited solids 18 with a further treatment fluid is desired, this further treatment fluid may be introduced into the reservoir 9 at the stage represented by FIG. 7 so as to flow to the buffer chamber 10 during the following stage represented by FIG. 8, and so on.

Figure 9:
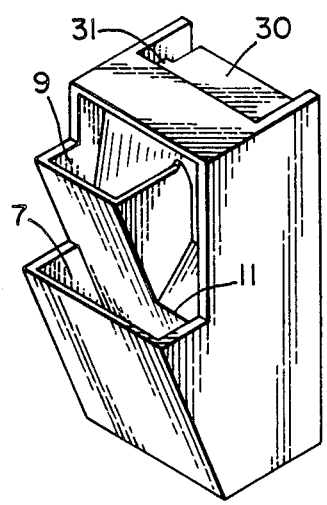
FIG. 9 is a front three-quarter perspective view of another form of sample handling unit embodying the invention.
Figure 10:
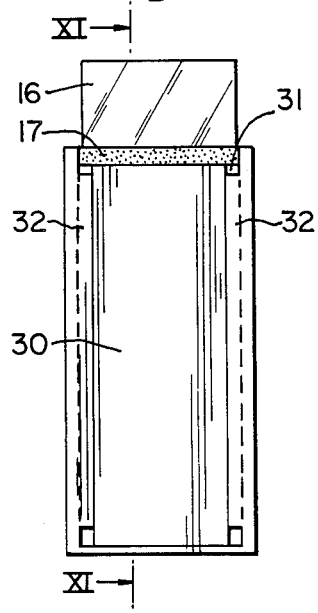
FIG. 10 is a rear elevation of the unit of FIG. 9 showing a slide and filter card installed therein.
Figure 11:
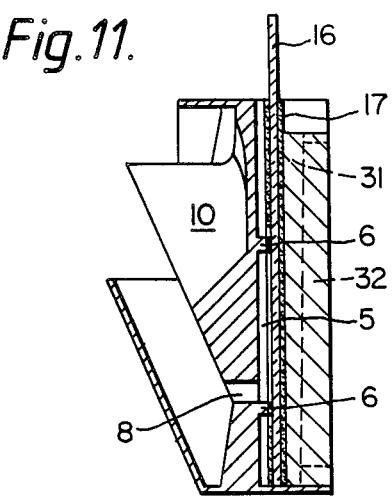
FIG. 11 is a vertical sectional view of the sample handling unit with installed slide and filter card as seen on the line XI—XI of FIG. 10.

Another form of sample handling unit embodying the invention is illustrated in FIGS. 9 to 11. The sample handling unit shown in these Figures is generally similar to that of FIGS. 1 to 4, and parts thereof corresponding with parts of the unit of FIGS. 1 to 4 are accordingly given the same references. However the sample handling unit of FIGS. 9 to 11 differs in the absence of a hinged rear door and its substitution by a back-plate 30 that has tapered lateral flanges 31 engaging with complementary ramped ribs 32 on the body part 2 of the sample unit so as to generate a forward thrust on a filter card-enwrapped slide 16 disposed between the back-plate 30 and the rear of the body part 2, as the back-plate is slid into place.

A sample handling unit embodying the invention may also incorporate two or more treatment fluid reservoirs equivalent to the reservoir 9 of the embodiments illustrated in FIGS. 1 to 4 and 9 to 11, respectively, with associated buffer chambers 10 and weirs 11 so arranged as to provide for, e.g., a second treatment fluid being transferred from a second treatment fluid reservoir successively via first, second and third buffer chambers with intervening weirs and thence to the sample reservoir over a weir equivalent to the weir 11 so as to reach the well of the sample reservoir when the centrifuge comes to rest at the conclusion of treatment of a deposited solids layer with a first treatment fluid by the sequence of steps that have been described in relation to FIGS. 5 to 8. For compactness, the second buffer chamber of such an arrangement may be constituted by the first treatment fluid reservoir, in the manner now to be described in connection with FIGS. 14 to 16.

Figure 14:
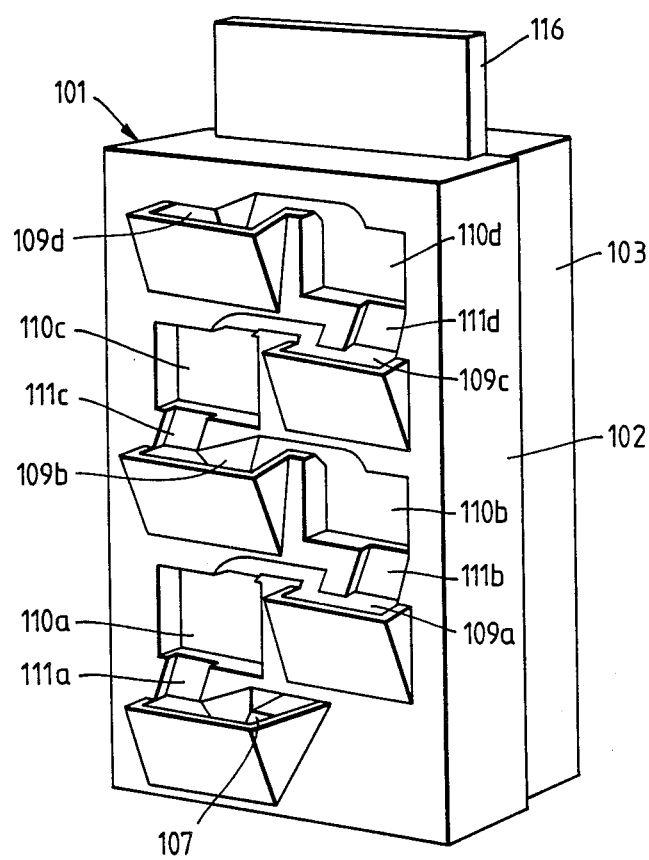

Thus, FIGS. 14 to 16 illustrate a sample handling unit 101 having provision for four successive treatments of deposited solids with treatment fluids placed in respective reservoirs provided in the body of the unit. The unit 101 has generally the same basic configuration as that of FIGS. 1 to 4 and thus comprises a body having a part 102 fitted with a hinged rear door 103 that in place of the cruciform pressure pad 12 of the unit 1 has a vertical rib 112 providing the same function, that of holding a filter card-enwrapped slide 116 firmly against the rear end of a wall 106 defining a deposition chamber 105.

As in the previously described embodiments, an aperture in the filter card 117 defines a deposit-receiving area on the slide 116 and the card seals against the end of wall 106. However, because of the greater fluid-absorbing capacity required to accommodate the liquid of the sample and up to four treatment fluid portions, the absorbency of the filter card 117 is supplemented by a packing 117a of absorbent wadding or the like housed in the rear door 103 so as to contact the filter card 117 behind the slide 116.

Also as in the previously described embodiments, the body part 102 is formed with a sample reservoir 107 that communicates with the deposition chamber 105 through a slot 108 and provides a well 120 for retention of fluid (sample or treatment fluid) when normal gravity acts on the unit.

The sample handling unit of FIGS. 14 to 16 is mainly distinguished by its body part 102 having four treatment fluid reservoirs 109a, 109b, 109c and 109d, respectively, arranged in an extended cascade flow path comprising also buffer chambers 110a, 110b, 110c and 110d with weirs 111a, 111b, 111c and 111d respectively associated therewith.

In use of the sample handling unit 101 of FIGS. 14 to 16, the unit assembled with slide 116, filter card 117 and packing 117a would be fitted to a centrifuge head in the same way as described for the unit 1 of FIGS. 1 to 4. Fluent sample material would be placed in sample reservoir 107 to be retained in well 120, while up to four treatment fluids would be placed in reservoirs 109a to 109d in the order in which the respective fluids were to be applied to solids deposited on the receiving surface of slide 116: that is, the first treatment fluid would be placed into reservoir 109a, the second into reservoir 109b, the third into reservoir 109c; and the fourth into reservoir 109d.

Upon first running-up the centrifuge to establish the artificial gravitational field, the sample in well 120 would be transferred via slot 108 to the deposition chamber 105 and thence formed as a layer on the receiving surface of the slide, as described in connection with FIG. 6. Concurrently, the treatment fluids in the reservoirs 109a to 109d would be respectively transferred to the associated buffer chambers 110a to 110d but retained therein by the respective weirs 111a to 111d.

Subsequently, upon reduction of the artificial gravitational field and reassertion of normal gravity, treatment fluid in the buffer chamber 110a would flow over weir 111a into reservoir 107 to be held in the well 120 thereof, in the manner described in relation to FIG. 7. However, concurrently with this transfer, the treatment fluids in buffer chambers 110b, 110c and 110d would flow over the respective weirs 111b, 111c and 111d to be retained, respectively in the reservoirs 109a, 109b and 109c. Thus as a consequence of running-up the centrifuge and thereafter slowing it, the first treatment fluid is transferred from reservoir 109a to the well 120 of reservoir 107 (ready to be applied to the deposited solids on the slide 116 when the centrifuge is run-up again to restore the artificial gravitational field), while the second treatment fluid is transferred from reservoir 109b to reservoir 109a; the third treatment fluid is transferred from reservoir 109c to reservoir 109b; and the fourth treatment fluid is transferred from reservoir 109d to reservoir 109c.

Accordingly, it can be seen that successive cycles of running-up the centrifuge and then slowing it so as to cause cyclic applications of artificial and normal gravity result firstly in the deposition of solids of a sample on the receiving surface of the slide 116, followed by successive treatments of those deposited solids with the treatment fluids placed initially in the reservoirs 109a to 109d.

A sample handling unit embodying the invention may be fitted to a centrifuge head in any convenient manner. Thus a centrifuge head may be fitted with suitably shaped receiving buckets to accommodate a set of sample handling units, each such bucket having, for instance, an upright outboard wall to be engaged by the rear door or back-plate of the sample handling unit, as the case may be, and, preferably, a ramped inboard wall to co-operate with the front face of the body of the sample handling unit and thereby wedge the latter firmly in place in the bucket. Desirably, the outboard wall of the bucket is formed with a notch or recess to be engaged with the tang 15 of the rear door, or with an equivalent protrusion, whereby such tang or protrusion will serve to prevent any vertical movement of the sample handling unit relative to the bucket when the artificial gravitational field is acting on the sample handling unit during centrifugation.

Figure 12:
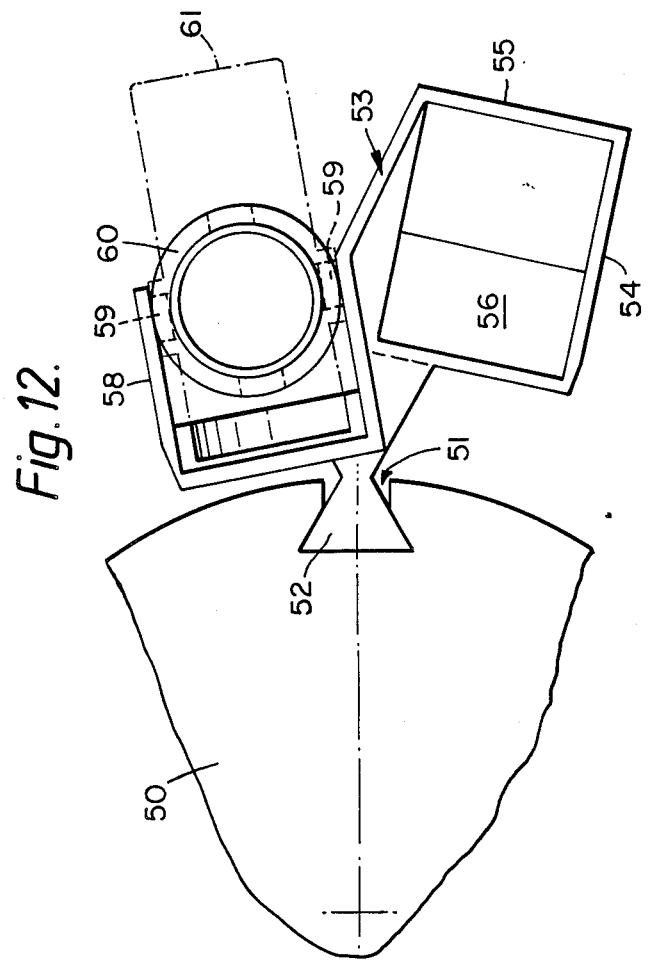
FIG. 12 is a fragmentary plan view of the head of a centrifuge fitted with a carrier including a bucket to receive a sample handling unit constructed as in FIGS. 1 to 8 or FIGS. 9 to 11.
Figure 13:
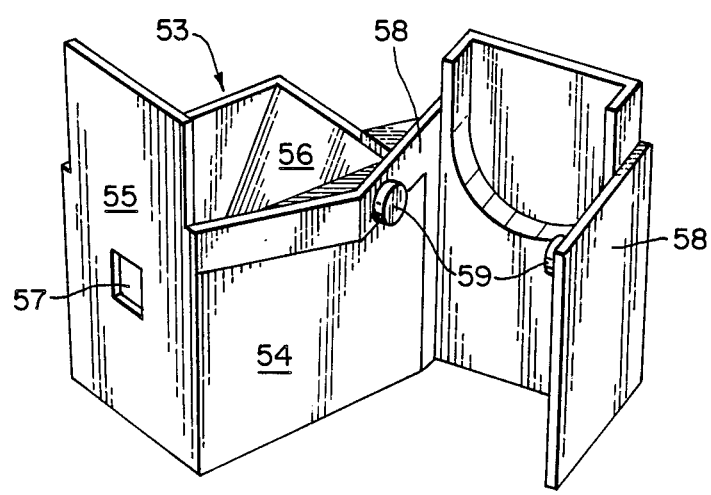
FIG. 13 is a rear three-quarter perspective view of the carrier shown in FIG. 12.

FIGS. 12 and 13 illustrate, in fragmentary plan view and in perspective, a bucket and sample tube carrier that may be fitted to a centrifuge head to accommodate sample handling units of the construction illustrated in FIGS. 1 to 4, in FIGS. 9 to 11 or in FIGS. 14 to 16, and also to provide for a pre-treatment of, e.g., a cell suspension in a sample tube prior to a sample of the suspension being transferred to the sample handling unit of the sample chamber in the bucket.

Thus, in FIG. 12 the centrifuge head is represented at 50 and has dovetail slots at intervals around its periphery, only one such slot being shown at 1. A carrier with a complementary dovetail tongue 52 includes a bucket 53 in the form of a frame 54 generally rectangular in plan and arranged relatively to the tongue 52 so that its outboard and inboard walls are perpendicular to a radius of the centrifuge head, the outboard wall 55 being parallel to the axis of rotation whereas the inboard wall 56 slopes downwardly and outwardly in a manner complementary to the front face of that portion of sample handling unit body 2 that constitutes the sample reservoir. The outboard wall 55 has a notch 57 to receive the tang 15 on the rear door 3 of a sample chamber of the configuration shown in FIGS. 1 to 4.

The carrier 53 also includes a yoke 58 having trunnions 59 to engage notches in a collar 60 of a sample tube indicated diagrammatically in FIG. 12 and that is thereby enabled to swing to the attitude indicated in broken lines 61 under the influence of the artificial gravitational field resulting from running of the centrifuge.

The details of the construction of the carrier 53 are described in patent application Ser. No. 871,530 filed June 6, 1986.

In the embodiments of the sample handling unit so far described, a sample reservoir 7, 107 is provided for retention of sample material prior to application of the artificial gravitational field that causes flow of material from the well 20 or 120 of the sample reservoir to the deposition chamber 5 or 105. Moreover, in these embodiments also, the treatment fluid flow paths to the deposition chamber include the sample reservoir in each case. Retention of sample material in the sample reservoir until centrifugation commences is desirable for reasons that have been explained. For analogous reasons it will usually be desirable to hold treatment fluid(s) out of contact with the deposited solids until artificial gravity is applied to cause the treatment fluid to form a regular layer on the deposited solids; and in general to enable better control of the application of treatment fluid(s).

However, where such considerations do not apply, the sample reservoir may be omitted, provision being made for sample material to be loaded directly into the deposition chamber with the sample handling unit subject only to normal gravity.

Likewise, even in cases in which a sample reservoir is provided, the flow path(s) from treatment fluid reservoir(s) may lead directly to the deposition chamber. For instance, in the embodiment of FIGS. 1 to 4, treatment fluid flowing over the weir 11 might be ducted directly into the deposition chamber 5—e.g., through a suitable slot in the body part 2—instead of into the sample reservoir 7.

FIGS. 17 to 20 illustrate a modification of the sample handling unit of FIGS. 1 to 4 in which the well 20 of the sample reservoir 7 is omitted, the sample chamber of the modified embodiment having only a vestigial reservoir 207 serving merely to provide a convenient entry to the deposition chamber, via slot 208, for sample material and for treatment fluid flowing over a weir 211. FIGS. 17 to 20 correspond with FIGS. 5 to 8, respectively, and show in similar manner to those Figures how sample material 221 and treatment fluid 222 is disposed at successive stages in the use of the modified sample handling unit. As is apparent, sample material placed into the vestigial reservoir 207 when the unit is at rest (FIG. 17) forms a pool at the bottom of the deposition chamber 205, being spread as a layer on the slide 216 when artificial gravity 223 is applied (FIG. 18) to leave a deposit of solids 218 when the liquid of the sample has been absorbed and the unit is once more at rest (FIG. 19). Meanwhile, treatment fluid 222 placed into reservoir 209 (FIG. 17) is transferred first to buffer chamber 210 when artificial gravity is applied (FIG. 18) and thence flows over weir 211 to form a pool 228 at the bottom of the deposition chamber 205 when the unit is brought to rest (FIG. 19). Thereafter the fluid spreads as a layer 219 over the deposited solids 218 when artificial gravity is once again applied (FIG. 20), and is then absorbed by the filter card 217 when it has performed its treatment function.

It is plain that the sample handling units of FIGS. 9 to 11 and FIGS. 14 to 16 could be modified in similar manner to omit the wells 20, 120, of their respective sample reservoirs.

We claim:

1. For centrifugation apparatus, a sample handling unit comprising a body having means therein defining:
   a sample chamber adapted to receive fluent sample material when the body is in a vertically arranged position for centrifugation and having a deposition chamber with an open side,
   means for receiving a deposit receiving element with a deposit receiving surface juxtaposed to the open side of the deposition chamber to receive thereon sample material under the influence of an artificial gravitational field effected by centrifugation,
   a treatment fluid reservoir having an upper opening and adapted to receive retain treatment fluid when the body is in a vertically arranged position for centrifugation and in the absence of an artificial gravitational field,
   means through which sample material may be supplied to the sample chamber through and upper opening therein without passages through the treatment fluid reservoir,
   a buffer chamber constructed and arranged relatively to the treatment fluid reservoir to receive therefrom treatment fluid therein under the influence of an artificial gravitational field effected by centrifugation, and
   flow path means including a weir communicating the buffer chamber with the sample chamber constructed and arranged to retain treatment fluid in the buffer chamber while said artificial gravitational field is maintained by to allow flow of treatment fluid in said flow path means when said artificial gravitational field is reduced.

2. The sample handling unit of claim 1, in which the said body further has therein means defining a sample reservoir arranged and constructed within the sample chamber to receive and retain fluent material, in the absence of an artificial gravitational field, and having flow path connection to said deposition chamber such as to allow transfer of fluent material from the sample reservoir to the deposition chamber only under the influence of an artificial gravitational field.

3. The sample handling unit of claim 2, in which said body has means therein defining at least one additional treatment fluid reservoir; at least one additional buffer chamber constructed and arranged relative to said additional treatment fluid reservoir, to receive treatment fluid therefrom under the influence of the artificial gravitational field; and at least one additional flow path means including an additional weir communicating with said additional buffer chamber and constructed and arranged to retain treatment fluid while the artificial field is maintained but allow treatment fluid to flow in said additional flow path means when said field is reduced, said flow path means and additional flow path means being arranged so that treatment fluids in the respective treatment fluid reservoirs must traverse different numbers of weirs to reach the deposition chamber.

4. The sample handling unit of claim 1, in which said body is a moulding of plastics material.

5. The sample handling unit of claim 4, in which said means for receiving a deposit receiving element comprises a rear door hinged and so constructed that when closed it can secure a filter card-enwrapped slide with a deposit-receiving area of the slide exposed and juxtaposed to the open side of said deposition chamber.

6. The sample handling unit of claim 1, in which said body further has therein means defining a vestigial reservoir arranged and constructed within the sample chamber to receive fluent material, and having flow path connection to the deposition chamber for the transfer thereto of fluent material in the absence of an artificial gravitational field.

7. The sample handling unit of claim 6, in which said body has means therein defining at least one treatment fluid reservoir; at least on additional buffer chamber constructed and arranged relative to said additional treatment fluid reservoir to receive treatment fluid therefrom under the influence of the artificial gravitational field; and at least one additional flow path means including an additional weir communicating with said additional buffer chamber and constructed and arranged to retain treatment fluid while the artificial filed is maintained by allow treatment fluid to flow in said additional flow path means when said filed is reduced, said flow path means and additional flow path means being arranged so that treatment fluids in the respective treatement fluid reservoirs must traverse different numbers of weirs to reach the deposition chamber.

8. The sample handling unit of claim 7, in which said flow path means comprises a flow path extending from the buffer chamber associated with a first said treatment fluid reservoir to an additional treatment fluid reservoir; whereby said treatment fluid reservoirs are consecutively linked with one another and to said sample reservoir by said flow path.

* * * * *